(12) United States Patent
Novatzky et al.

(10) Patent No.: US 8,229,193 B2
(45) Date of Patent: Jul. 24, 2012

(54) SYSTEM AND METHODS FOR APPLYING IMAGE PRESENTATION CONTEXT FUNCTIONS TO IMAGE SUB-REGIONS

(75) Inventors: Benjamin D. Novatzky, Oak Park, IL (US); Joseph Carroll, Arlington Heights, IL (US)

(73) Assignee: General Electric Company, Schenectady, NY (US)

( * ) Notice: Subject to any disclaimer, the term of this patent is extended or adjusted under 35 U.S.C. 154(b) by 994 days.

(21) Appl. No.: 12/203,682

(22) Filed: Sep. 3, 2008

(65) Prior Publication Data
US 2010/0054556 A1  Mar. 4, 2010

(51) Int. Cl.
*G06K 9/00* (2006.01)
(52) U.S. Cl. ........................................ 382/128
(58) Field of Classification Search ............ 382/128
See application file for complete search history.

(56) References Cited

U.S. PATENT DOCUMENTS

| | | | |
|---|---|---|---|
| 5,467,441 A * | 11/1995 | Stone et al. | 345/619 |
| 5,542,003 A | 7/1996 | Wofford | |
| 6,553,139 B1 * | 4/2003 | Kaup | 382/167 |
| 6,735,330 B1 | 5/2004 | Van Metter et al. | |
| 7,349,564 B2 * | 3/2008 | Zijp et al. | 382/131 |
| 2007/0130525 A1 * | 6/2007 | Murphy et al. | 715/747 |
| 2008/0089572 A1 * | 4/2008 | Yamano et al. | 382/131 |
| 2010/0260395 A1 * | 10/2010 | Cable | 382/128 |
| 2011/0040168 A1 * | 2/2011 | Arnaud et al. | 600/407 |

* cited by examiner

*Primary Examiner* — Christopher Mahoney
(74) *Attorney, Agent, or Firm* — Hanley, Flight and Zimmerman, LLC

(57) ABSTRACT

System and methods for applying image presentation context functions to image sub-regions are disclosed. An example method includes displaying a first medical image in a user interface, receiving a selection of a first image sub-region within the first medical image, receiving a selection of a first image presentation context function and a selection of an amount of a parameter of the first image presentation context function for the selected first image sub-region, applying the received first image presentation context function by the amount of the received parameter of the first image presentation context function to the received first image sub-region, and displaying the first sub-region with the applied first image presentation context function within the first medical image.

37 Claims, 8 Drawing Sheets

SYSTEM AND METHODS FOR APPLYING IMAGE PRESENTATION CONTEXT FUNCTIONS TO IMAGE SUB-REGIONS

FIELD OF THE DISCLOSURE

This disclosure relates generally to dynamic display information and more particularly, to system and methods for applying image presentation context functions to image sub-regions in a picture archiving and communication system.

BACKGROUND OF THE INVENTION

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, and equipment. Personnel in a healthcare facility must manage a plurality of patients, systems, and tasks to provide quality service to patients. Healthcare personnel may encounter many difficulties or obstacles in their workflow.

Healthcare environments, such as hospitals or clinics, include clinical information systems, such as hospital information systems (HIS) and radiology information systems (RIS), and storage systems, such as picture archiving and communication systems (PACS). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy that are stored in a medical information system. Alternatively, medical personnel may enter new information, such as history, diagnostic, or treatment information, into a medical information system during an ongoing medical procedure.

A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools.

Picture archiving and communication systems (PACS) connect to medical diagnostic imaging devices and employ an acquisition gateway (between the acquisition device and the PACS), storage and archiving units, display workstations, databases, and sophisticated data processors. These components are integrated together by a communication network and data management system. A PACS has, in general, the overall goals of streamlining health-care operations, facilitating distributed remote examination and diagnosis, and improving patient care.

A typical application of a PACS system is to provide one or more medical images for examination by a medical professional. For example, a PACS system can provide a series of x-ray images to a display workstation where the images are displayed for a radiologist to perform a diagnostic examination. Based on the presentation of these images, the radiologist can provide a diagnosis. For example, the radiologist can diagnose a tumor or lesion in x-ray images of a patient's lungs.

Typically, data stored in a PACS is stored as Digital Imaging and Communications in Medicine (DICOM) data. DICOM is a standard for image and information transmission. DICOM relates to the transfer of electronic data between medical diagnostic and imaging systems. The DICOM protocol may be employed in communication between medical devices and PACS. The DICOM standard enumerates a command set, data formats, interface specifications, communication protocols, and command syntax. However, the DICOM standard does not specify details of implementation. DICOM sets forth Information Objects (types of data, such as computerized tomography, magnetic resonance, x-ray, ultrasound, etc.), Service Classes (actions with data, such as send, receive, print, etc.), and data transmission protocols. The Service Class User (SCU) protocol governs use of the DICOM service. The Service Class Provider (SCP) protocol governs the provider of the DICOM service.

Current PACS systems use general techniques known as hanging protocols to format display or layout of images. Hanging protocols allow a user to display images based on modality, anatomy, and procedure. Hanging protocols present a perspective or view to a user, such as a radiologist. Images may be grouped according to characteristics such as DICOM series or series number.

Additionally, PACS systems attempt to prepare images for viewing by users by applying a series of processing steps or functions included in a Default Display Protocol (DDP). A DDP is a default workflow that applies a series of image processing functions to image data to prepare the image data for presentation to a user on a particular monitor configuration. DDPs typically include processing steps or functions that are applied before any diagnostic examination of the images. A DDP may be based on a type of imaging modality used to obtain the image data, for example. In general, a DDP attempts to present image data in a manner most useful to many users.

With increasing volumes of examinations and images, a reduction of radiologists and mounting pressures on improved productivity, radiologists and other healthcare personnel are in need of image processing or display workflow enhancements that alleviate rote, repetitive tasks. Currently, medical images are displayed using only a single image presentation context (IPC). An IPC comprises functions that alter the presentation of an image such as, for example, zoom, pan, grayscale, invert color, filter, contrast, etc. Different types of anatomy have different optimal IPCs for viewing structures or tissue. For example, in an x-ray image of a chest, bones are clearly shown when a darker contrast is applied to the x-ray image while tissue is clearly shown when a lighter contrast is applied to the x-ray image. As a result, radiologists, physicians, or healthcare personnel must switch back and forth between medical images of the same structure with different IPCs for making a medical diagnosis. This switching between multiple images is inefficient and relies on the ability of healthcare personnel to remember what an image looked like in a different IPC.

Alternatively, healthcare personnel may load multiple images with different IPCs of the same structure on to a single or multiple display screens. However, this requires healthcare personnel to glance back and forth between the multiple images to perform comparisons for making a diagnosis. The inefficient manner of viewing multiple images causes the healthcare personnel to spend extra time viewing images and comparing information between two or more images. This extra time reduces their ability to perform other tasks such as treating patients or examining medical information for other patients. Additionally, for presentations or display publications healthcare personnel must print multiple versions of a structure with different IPCs in order to display different anatomies in the structure.

BRIEF SUMMARY OF THE INVENTION

Example system and methods for applying image presentation context functions to image sub-regions are described. In one example, a method includes displaying a first medical image in a user interface. Then, the method includes receiving a selection of a first image sub-region within the first medical image and receiving a selection of a first image presentation context function and a selection of an amount of a parameter of the first image presentation context function for the selected first image sub-region. Additionally, the example method includes applying the received first image presentation context function by the amount of the received parameter of the first image presentation context function to the received first image sub-region and displaying the first sub-region with the applied first image presentation context function within the first medical image.

In another example, a system includes an input receiver to receive a selection of a first image sub-region within the first medical image and to receive a selection of a first image presentation context function and a selection of an amount of a parameter of the first image presentation context function for the selected first image sub-region. Additionally, the example system includes an image presentation context generator to apply the received first image presentation context function by the amount of the received parameter of the first image presentation context function to the received first image sub-region.

Certain implementations provide a machine accessible medium having instructions stored thereon for execution on a processor. The instructions that, when executed, cause a machine to display a first medical image in a user interface. Then, the instructions when executed, cause a machine to receive a selection of a first image sub-region within the first medical image and receive a selection of a first image presentation context function and a selection of an amount of a parameter of the first image presentation context function for the selected first image sub-region. Furthermore, the instructions that, when executed, cause a machine to apply the received first image presentation context function by the amount of the received parameter of the first image presentation context function to the received first image sub-region and display the first sub-region with the applied first image presentation context function within the first medical image.

Figure 1:
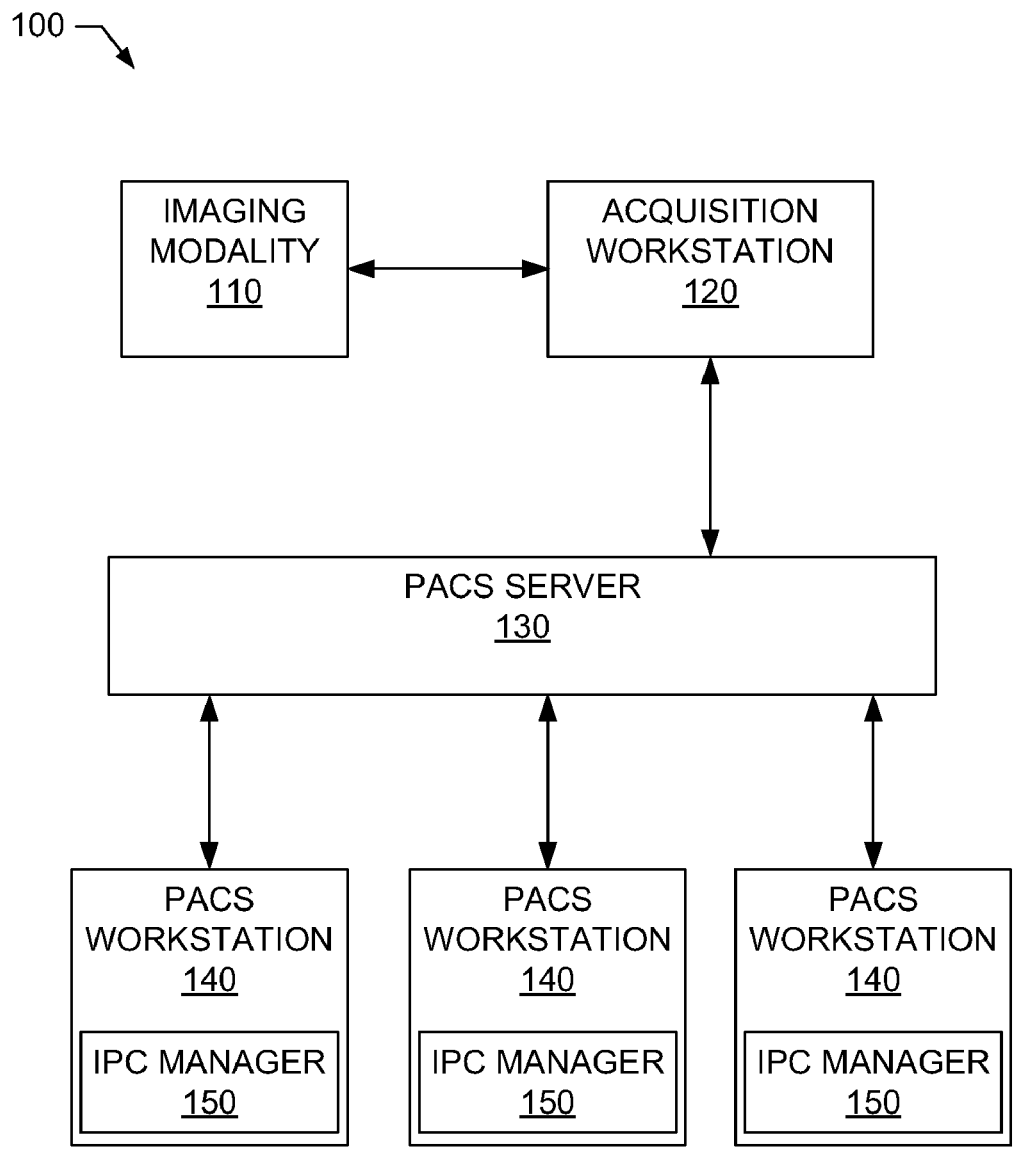
FIG. 1 shows a picture archiving and communication system including an example image presentation context (IPC) manager.

The foregoing summary, as well as the following detailed description of certain implementations of the example IPC manager, will be better understood when read in conjunction with the appended drawings. For the purpose of illustrating the IPC manager, certain implementations are shown in the drawings. It should be understood, however, that the example IPC manager is not limited to the arrangements and instrumentality shown in the attached drawings.

DETAILED DESCRIPTION OF THE INVENTION

FIG. 1 illustrates a Picture Archiving and Communication System (PACS) 100 including an example IPC manager 150. Additionally, the PACS system 100 includes an imaging modality 110, an acquisition workstation 120, a PACS server 130, and one or more PACS workstations 140. The system 100 may include any number of imaging modalities 110, acquisition workstations 120, IPC managers 150, PACS server 130, and PACS workstations 140 and is not in any way limited to the example implementation of system 100 illustrated in FIG. 1. The components of the system 100 may communicate via wired and/or wireless communication, for example, and may be separate systems and/or integrated to varying degrees, for example.

In operation, the imaging modality 110 obtains one or more images of a patient anatomy. The imaging modality 110 may include any device capable of capturing an image of a patient anatomy such as a medical diagnostic imaging device. For example, the imaging modality 110 may include an X-ray imager, ultrasound scanner, magnetic resonance imager, or the like. Image data representative of the image(s) is communicated between the imaging modality 110 and the acquisition workstation 120. The image data may be communicated electronically over a wired or wireless connection, for example.

In an embodiment, the acquisition workstation 120 may apply one or more preprocessing functions, for example, to the image data in order to prepare the image for viewing on a PACS workstation 140. For example, the acquisition workstation 120 may convert raw image data into a DICOM standard format or attach a DICOM header. Preprocessing functions may be characterized as modality-specific enhancements, for example (e.g., contrast or frequency compensation functions specific to a particular X-ray imaging device), applied at the beginning of an imaging and display workflow. The preprocessing functions differ from processing functions applied to image data in that the processing functions are not modality specific and are instead applied at the end of the imaging and display workflow (for example, at a display workstation 140).

The image data may then be communicated between the acquisition workstation 120 and the PACS server 130. The image data may be communicated electronically over a wired or wireless connection, for example.

The PACS server 130 may include computer-readable storage media suitable for storing the image data for later retrieval and viewing at a PACS workstation 140. The image data may be stored as a group of images (e.g., a stack of images) from one or more instances of images generated by the imaging modality 110. The PACS server 130 may also include one or more software applications for additional processing and/or preprocessing of the image data by one or more PACS workstations 140.

One or more PACS workstations 140 are capable of or configured to communicate with the server 130. The PACS workstations 140 may include a general purpose processing circuit, a PACS server 130 interface, a software memory, and/or an image display monitor, for example. The PACS server 130 interface may be implemented as a network card connecting to a TCP/IP based network, but may also be implemented as a parallel port interface, for example.

The PACS workstations 140 may retrieve or receive image data from the server 130 for display to one or more users. For example, a PACS workstation 140 may retrieve or receive image data representative of a computed radiography (CR) image of a patient's chest. A radiologist or user may then examine the image for any objects of interest, such as tumors, lesions, etc., for example.

The PACS workstations 140 may also be capable of or configured to apply IPC processing functions to image data. For example, a user may desire to apply IPC functions to enhance features within an image representative of the image data. IPC processing functions may therefore adjust an image of a patient anatomy in order to ease a user's diagnosis of the image. Such IPC functions may include any software-based application that may alter a visual appearance or representation of image data. For example, an IPC function can include any one or more of flipping an image, zooming in an image, panning across an image, altering a window and/or level in a grayscale representation of the image data, and altering a contrast and/or brightness an image.

In an embodiment, the PACS system 100 may provide one or more perspectives for viewing images and/or accessing applications at a PACS workstation 140. Perspectives may be provided locally at the PACS workstation 140 and/or remotely from the PACS server 130. In operation, for example, a user, such as a radiologist, selects a set of images, such as screening mammogram images, chest screening images and/or other computed radiography (CR), digital radiography (DR), and/or digital x-ray (DX) screening images, to review at a PACS workstation 140. The images may be displayed in a default perspective and/or a customized perspective, for example.

The PACS workstations 140 may retrieve or receive image data from the PACS server 130 for display to one or more users. For example, a PACS workstation 140 may retrieve or receive image data representative of a computed radiography image of a patient's chest. A radiologist may then examine the image as displayed on a display device for any objects of interest such as, for example, tumors, lesions, etc.

The PACS workstations 140 are also capable of or configured to retrieve and/or receive one or more hanging protocols from server 130. For example, a default hanging protocol may be communicated to PACS workstation 140 from server 130. A hanging protocol may be communicated between server 130 and a PACS workstation 140 over a wired or wireless connection, for example.

In general, PACS workstations 140 may present images representative of image data retrieved and/or received from server 130. PACS workstations 140 may present the images according to a hanging protocol. As described above, a hanging protocol is a set of display rules for presenting, formatting and otherwise organizing images on a display device of a PACS workstation 140. A display rule is a convention for presenting one or more images in a particular temporal and/or spatial layout or sequence. For example, a hanging protocol may include a set of computer-readable instructions (or display rules, for example) that direct a computer to display a plurality of images in certain locations on a display device and/or display the plurality of images in a certain sequence or order.

A hanging protocol may direct, for example, a PACS workstation 140 to display an anterior-posterior (AP) image adjacent to a lateral image of the same anatomy. In another example, a hanging protocol may direct PACS workstation 140 to display the AP image before displaying the lateral image. In general, a hanging protocol dictates the spatial and/or temporal presentation of a plurality of images at PACS workstation 140.

A hanging protocol may differ from a default display protocol (DDP). In general, a DDP is a default workflow that applies a series of image processing functions to image data. The image processing functions are applied to the image data in order to present an image (based on the image data) to a user. The image processing functions alter the appearance of image data. For example, an image processing function may alter the contrast level of an image.

DDPs typically include processing steps or IPC functions that are applied before any diagnostic examination of the images. For example, IPC processing functions may be applied to image data in order to enhance features within an image (based on the image data). Such IPC functions can include any software-based application that may alter a visual appearance or representation of image data. For example, an IPC function can include any one or more of flipping an image, zooming in an image, panning across an image, altering a window and/or level setting in a representation of the image data, and altering a contrast and/or brightness setting in a representation of the image data.

DDPs are usually based on a type of imaging modality used to obtain the image data. For example, image data obtained with a C-arm imaging device in general or a particular C-arm imaging device may have a same or similar DDP applied to the image data. In general, a DDP attempts to present image data in a manner most useful to many users. Conversely, applying a hanging protocol to image data does not alter the appearance of an image (based on the image data), but instead dictates how the image(s) is (are) presented, as described above.

The PACS Server 130 may store a plurality of hanging protocols and/or DDPs. The hanging protocols and/or DDPs that are stored at server 130 and have not yet been modified or customized are default hanging protocols/DDPs. A default hanging protocol and/or DDP may be selected from a plurality of default hanging protocols and/or DDPs based on any number of relevant factors Such as, for example, a manual selection, a user identity, and/or pre-processing of the image data.

Specifically, a default hanging protocol and/or DDP may be selected based on a manual selection simply by communicating the default protocol once a user has selected that particular protocol. The user may make the selection, for example, at a PACS workstation 140. Selection of a hanging protocol on a PACS workstation 140 may be based on a plurality of criteria, such as a number of connected displays, a modality, an anatomy, and a procedure, for example. The hanging protocols with perspectives/views may use one or more criteria to select a protocol for display. For example, a modality, an anatomy or body part, a procedure, and/or a default view for a display configuration, may be used to select an appropriate display protocol. For example, a display protocol includes a perspective/view with multiple options depending upon monitor configuration.

Perspectives are views or layouts indicating visual component positioning and interactions between images and/or applications based on workflow, for example. Medical perspectives may be used to create a plurality of benefits for users. Furthermore, for example, perspectives provide an ability to store or "remember" specific workflow steps. Perspectives provide a mechanism to save and display information relevant to a particular user, group, and/or function, for example.

The PACS server 130 of FIG. 1 is communicatively coupled to the example IPC managers 150 located within PACS workstations 140 to manage the display of sub-regions within medical images. While FIG. 1 shows a single IPC manager 150 within each respective PACS workstation 140, some PACS workstations 140 may not include an IPC manager 150. Alternatively, the IPC manager 150 may be included within the PACS server 130 such that one or more IPC managers 150 on the PACS server 130 may process different medical images for one or more PACS workstations 140.

The example IPC manager 150 may implement any one of the hanging protocols, perspectives, and/or DDPs to display one or more medical images in a user interface displayed on the PACS workstations 140. The IPC manager 150 enables a user to apply different IPCs to one or more sub-regions within a medical image on a PACS workstation 140. The medical image may be generated during one or more imaging procedures in the imaging modality 110. Applying multiple IPCs to different sub-regions within a single medical image results in more optimal or improved viewing of different anatomies. This provides a thorough comparison of anatomies of different densities and/or compositions in a single medical image. Additionally, the IPC manager 150 enables a user to toggle between different IPC function parameters and/or different IPC functions within a sub-region. Furthermore, the IPC manager 150 provides an ability to apply one or more IPC functions to a sub-region.

IPCs include functions that modify a presentation of an image. IPC functions include, zoom/pan functions, window center/width functions (WC/WW), image filtering functions, grayscale functions, invert color functions, contrast functions, and/or any other type of image modification function that changes an appearance of an image. Each IPC function includes parameters for defining an amount of that IPC function to apply to an image. For example, the zoom function includes parameters for a magnification amount (e.g., 25%, 200%, etc.) applied to an image sub-region. Parameters of the IPC functions include numeric values, Boolean values, and/or text description values. Tlhe parameter amounts for each function may be defined by a system developer and/or by a user. For example, a user may set the default amount for a WC/WW IPC function for the optimal display of bone structures. Additionally, the parameters may be specified by perspectives, hanging protocols, DDPs and/or any other type of software input (e.g., machine accessible medium).

IPC functions are used in imaging systems for displaying different anatomies of a single structure. In a single medical image, different anatomies may have different optimal viewing characteristics due to natural differences in composition, density, and/or appearance. For example, tissue on an x-ray image is clearly visible when a brighter contrast is applied to the x-ray image while bone on the same x-ray image is clearly visible when a darker contrast is applied to the x-ray image. In another example, a user may need to zoom into a particular region of a medical image to view a small growth. In yet another example, a user may need to convert portions of a color medical image to grayscale to determine an outline of an anatomy.

Currently, medical images are displayed with only a single IPC. For example, an x-ray image of an arm can only be displayed with a single contrast level. As a result, users must switch back and forth between medical images of the same structure with different IPCs for making a medical diagnosis. This switching between multiple images is inefficient and relies on the ability of a user to remember what an image looked like in a different IPC. Alternatively, the user may load multiple images with different IPCs of the same structure on to a single or multiple display screens. However, this requires the user to glance back and forth between the multiple images to perform comparisons for making a diagnosis. The example IPC manager 150 of FIG. 1 enables a user to apply multiple IPC functions to one or more sub-regions within the medical image. Displaying sub-regions increases the efficiency of medical image examinations, increases the clarity of the presentation of medical images when multiple medical conditions have to be displayed on a single image, and increases the accuracy of medical diagnoses.

The example IPC manager 150 may be activated when a user opens a user interface to display medical images on a PACS workstation 140. Alternatively, the IPC manager 150 may be activated in an already open user interface by a user inputting a hotkey from an input device and/or by a user selecting an icon in the user interface corresponding to the IPC manager 150. Furthermore, a user defined and/or default hanging protocol (and/or perspective) may activate the IPC manager 150 upon a user viewing certain types of images in the user interface.

The IPC manager 150 may use hanging protocols for specifying the size, shape, and/or location of a sub-region within a medical image and use DDPs for specifying the IPC functions and/or function parameters for each sub-region. For example, upon loading a medical image the IPC manager 150 may determine from a hanging protocol associated with the medical image that a circular shaped sub-region is located in a lower right section of the medical image. The IPC manager 150 then uses the DDP associated with the image to determine the contrast, zooming, and centering of the image within the sub-region. Alternatively, the IPC function parameter amounts may be applied from information within a DICOM header of a medical image. For example, a DICOM header for an image may allow for any one of three sets of WC/WW amounts (i.e., normal, hard, and soft) to be applied to that image.

The example IPC manager 150 enables one or more IPC functions to be applied to a sub-region. For example, a user may apply an IPC contrast function to lighten a sub-region and a zoom function to magnify a particular portion of the same sub-region. Additionally, the IPC manager 150 changes the display of a sub-region as a user toggles between two or more parameter amounts for a single IPC function. Furthermore, the example IPC manager 150 may enable a user to display multiple instances and/or copies of a sub-region with a different IPC function parameter amount applied to each instance. The instances may be displayed adjacent to the sub-region on a medical image and/or on the perimeter of the medical image. For example, a user may display a sub-region using three different zoom amounts. The first magnification is displayed in the sub-region while the second and third zoom amounts are displayed in copies of the sub-region next to the original sub-region.

In an example implementation of the IPC manager 150, a user identifies (e.g., select) a sub-region by defining an area within the medical image. The area is defined by placing a geometrical shape (e.g., circle, oval, rectangle, etc.) on the medical image. The area within the geometrical shape is the sub-region. A user may select a shape from the user interface on the PACS workstation 140 and position and/or size the shape on the medical image. Additionally, a sub-region is defined by a user drawing a perimeter of a shape on the medical image. The area inside the perimeter is the sub-region. The perimeter may be any shape capable of being drawn by a user. The shape may be drawn by moving a mouse cursor over the medical image, by keyboard inputs, or by moving an input device (i.e., a touchscreen pen or a finger) across a touchscreen displaying the medical image. Furthermore, the IPC manager 150 identifies a sub-region by a line extending from one point on the perimeter of the medical image to another point on the perimeter of the same medical image. The line may be a straight line or a line drawn by a user. The area on one side of the line specified by a user is the sub-region. The lines, curves, and/or shapes used by the IPC manager 150 to define a sub-region may be displayed as any shade of grey, any color, any type of dashed marking, and/or any marking thickness.

The example IPC manager 150 enables overlapping sub-regions and/or nested sub-regions. In the case of overlapping sub-regions, the IPC manager 150 may combine the IPC functions of each subregion and/or combine the parameters of each function of each sub-region. Additionally, in the case when two or more overlapping sub-regions include the same IPC function with different parameter amounts, the IPC manager 150 may prompt a user to select between the different amounts. In the case of nested sub-regions, the IPC manager 150 applies the IPC functions and/or IPC function parameters to each sub-region. Thus, the shape of the interior of the outer (e.g., higher) sub-region is defined by the perimeter of the inner sub-region. For example, if the sub-regions are circles, the outer sub-region is a ring with the interior defined by the IPC functions and area of the inner sub-region.

The IPC manager of FIG. 1 enables a user to lock sub-regions on a first medical image such that the user can load a second medical image and display the same sub-regions with the same IPC functions in the same locations on the second image. For example, a user may be scrolling through a stack of medical images stored on the PACS server 130. In a first image a user may define several sub-regions. The next few images in the stack display similar structures that have a similar shape to the first image. By locking one or more of the sub-regions displayed on the first image, the same sub-regions are defined and displayed when the user scrolls to the next images. Additionally, the sub-regions and the sub-region functions may be stored as templates in the IPC manager 150 and/or the PACS server 130. Thus, a user may load a stored template for other images and/or studies of similar procedures saving time from not having to redefine a particular sub-region.

Upon the IPC manager 150 displaying sub-regions in the user interface of PACS workstations 140, the IPC manager 150 may display an icon within each displayed sub-region indicating the applied IPC function type. The icons provide a visual indication to a user as to the types of functions applied to each sub-region. Additionally, the icons may be placed by the IPC manager 150 within the sub-region or adjacent to the sub-region. In cases where two or more IPC functions are applied to a sub-region, tile IPC manager 150 may display the corresponding number of icons. Additionally, a user may select an icon to access and/or change parameter amounts of the IPC function the icon represents. For example, a zoom IPC function may be indicated as an icon depicting a magnifying glass. A user may select the magnifying glass icon to change the zoom amount, disable the zoom IPC function, lock the IPC zoom function into the sub-region, and/or view the magnification amount.

Figure 2:
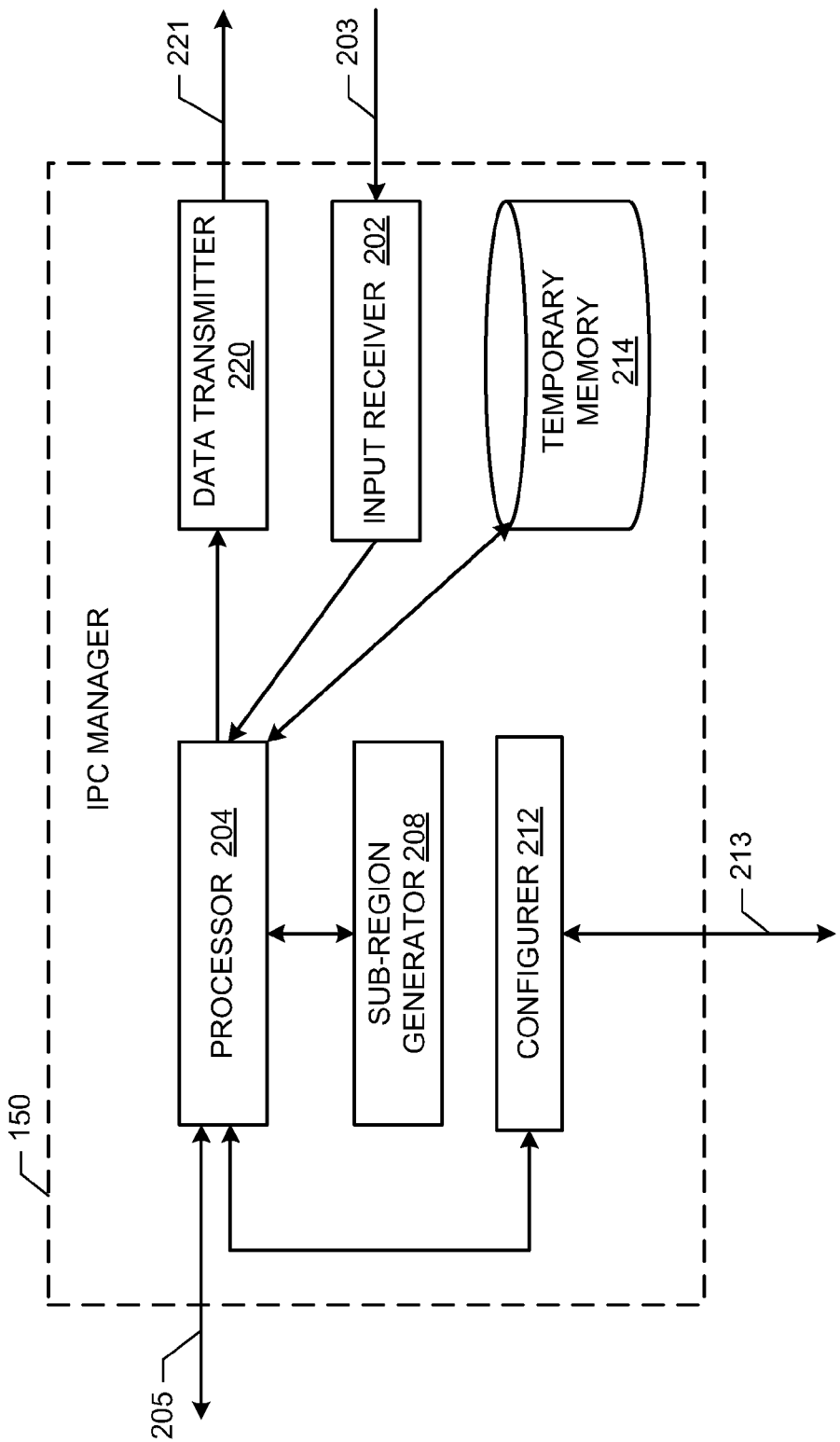
FIG. 2 shows a functional diagram of the example IPC manager of FIG. 1.

FIG. 2 shows a functional diagram of the example IPC manager 150 of FIG. 1 including an input receiver 202, a processor 204, a sub-region generator 208, a configurer 212, and a data transmitter 220. Additionally, the IPC manager 150 includes connections 203, 205, 213, and 221 to the PACS server 130. The connections 203, 205, 213, and 221 may include any types of electrical and/or mechanical connections to enable communication between the IPC manager 150 and the PACS server 130. The connections 203, 205, 213, and 221 may go through the respective PACS workstation 140 or alternatively, the connections 203, 205, 213, and 221 may directly connect to the PACS server 130. The IPC manager 150 receives instructions and data from the PACS server 130 via the connection 205 connected to the processor 204. The instructions may include activation instructions indicating, for example, that a PACS workstation 140 has opened a user interface for examining an image and/or a group of images. Additionally, the instructions may include deactivation instructions indicating the user has closed the user interface and/or deactivated the sub-region viewing application within the user interface. The instructions from the PACS server 130 may provide the IPC manager 150 with the network address of the PACS workstation 140 viewing an image and/or an image location in the memory of the PACS server 130.

The IPC manager 150 of FIG. 1 includes an example input receiver 202 to receive user generated inputs on the PACS workstations 140. The inputs may pass from the PACS workstations 140 to the PACS server 130 which then forwards the inputs via the connection 203 to the input receiver 202. Upon receiving the input, the input receiver 202 forwards the input to the processor 204. Alternatively, the input receiver 202 may receive inputs directly from the PACS workstations 140. The inputs received by the input receiver 202 include scrolling by a mouse cursor or a keyboard entry, selections of sub-regions, selections of IPC functions, selections of IPC function parameters, selections or specifications of IPC manager 150 configuration information, and/or any other type of image viewing inputs or sub-region creation inputs. For example, if a user specifies a sub-region by drawing a perimeter of a shape on a medical image using a mouse cursor, the input receiver 203 receives the digital data indicating the direction of the movement of the cursor. The input receiver 202 forwards this movement information to the processor 204 such that the processor 204 accumulates the number of movements by the cursor to define the corresponding sub-region on the medical image.

In addition to any number and/or type(s) of specialized hardware, firmware and/or logic to perform processing functions, the example processor 204 of FIG. 2 includes any number and/or type(s) of specialized and/or general purpose controller(s) and/or processing unit(s) capable of executing coded instructions. For example, the controller and/or processing unit may perform any number and/or type(s) of processing functions by carrying out and/or executing coded instructions present in a memory communicatively coupled and/or within the processor 204 (e.g., within a random-access memory (RAM), a read-only memory (ROM) and/or on-board memory of the processor 204).

The processor 204 manages the functions of the example IPC manager 150. The functions include processing inputs generated by users of the PACS workstations 140, loading an image and/or a group of images (e.g., an image stack) from the PACS server 130, saving an image to a temporary memory 214, coordinating the creation and management of sub-regions with the sub-region generator 208, processing user inputs specifying sub-region IPC functionality, transmitting sub-regions to be displayed within the user interface on the PACS workstations 140, transmitting a medical image for display within the user interface, and/or communicating configuration information to the PACS server 130. In an alternative implementation, the processor 204 may process an image and/or a group of images in the memory of the PACS server 130 without loading the image and/or group of images into the temporary memory 214 of the IPC manager 150.

The temporally memory 214 may be any number and/or type(s) of memories and/or memory devices including RAM and/or ROM memory The temporary memory 214 stores sub-region information for one or more images and/or groups of images. Additionally, the temporary memory 214 may store images and/or groups of images. Sub-region information includes sub-region shape, sub-region size, sub-region location on a medical image (e.g., x and y coordinates), IPC functions applied to the sub-region, IPC function parameter amounts, sub-region template information, and/or sub-region description information. The sub-region template information indicates if a sub-region is to be stored as a template and the types of medical images for applying the template sub-region. The temporary memory 214 may retain the sub-region information until a user ends an image viewing session on the PACS workstation 140 and/or may retain the sub-region information until a user manually removes the information from the user interface on the PACS workstation 140. Alternatively, the temporary memory 214 may store sub-region information until a specified time in which the IPC manager 150 deletes the information from the temporary memory 214.

The example sub-region generator 208 of FIG. 2 creates sub-regions within medical images and applies IPC functions to the images within the sub-regions. The processor 204 provides the sub-region generator 208 with instructions for sub-region creation including sub-region size and shape information, medical images, IPC functions to apply to the sub-regions, and/or the amounts of IPC functions applied to sub-regions. The sub-region generator 208 manages one or more sub-regions for each image and may apply one or more IPC function for each sub-region. Additionally, the sub-region generator 208 may change the applied IPC function parameter amounts as a user toggles the amounts in the user interface on a PACS workstation 140.

The sub-region generator 208 utilizes imaging tools for modification of the images within sub-regions. The imaging tools may be stored within the sub-region generator 208. Alternatively, the imaging tools may be stored within the configurer 212 and/or within the PACS server 130. The imaging tools implement IPC functions including zoom/pall functions, WC/WW functions, image filtering functions, grayscale functions, invert color functions, contrast functions, and/or any other type of image modification function that changes the appearance of an image. Additionally, the sub-region generator 208 may include functionality to enable a user to create IPC functions.

Upon creating sub-regions, the sub-region generator 208 inserts icons corresponding to the IPC functions applied to the sub-regions. For example, upon applying a pan function to a sub-region, the sub-region generator 208 inserts a pan icon within the sub-region and/or adjacent to the sub-region prior to transmitting the sub-region to the processor for display 204. Additionally, the sub-region generator 208 links IPC function options to the icons and/or user defined IPC function amounts to the icon. For example, if a user selects an icon, the processor 204 may query the sub-region generator 208 for the information to display in the tool tip of the selection.

The example sub-region generator 208 manages the lock functionality of the IPC manager 150. Upon receiving a selection to lock a sub-region for a group of images, the sub-region generator 208 applies the locked sub-region to images as they are loaded in the user interface of the PACS workstation 140 and/or as they are scrolled to by a user. The sub-region generator 208 may modify the shape and/or size of a sub-region to match any differences in image size and/or anatomy size between images in a group and the initial image with the sub-region lock.

The sub-region generator 208 manages IPC functions applied to overlapping sub-regions and nested sub-regions. In an example of overlapping sub-regions, the sub-region generator 208 may determine the sections of sub-regions that overlap and apply the IPC functions from both sub-regions to the overlapping region. If an IPC function is included in both sub-regions but each sub-region includes a different parameter amount, the sub-region generator 208 may prompt a user to select one of the parameter amounts, may average the parameter amount values, and/or select one of the parameter amounts. In an example of nested sub-regions, the sub-region generator 208 determines the areas of each sub-region and applies the IPC function(s) to the respective sub-regions.

In an example implementation of the sub-region generator 208, a user may load a medical image to a user interface on a PACS workstation 140. Upon activating the sub-region tool in the user interface, the PACS server 130 sends the input receiver 202 the loaded medical image. The received medical image is stored in the temporary memory 214 by the processor 204. As the user defines a sub-region area on the medical image, the input receiver 202 receives the selections and forwards them to the processor 204. The processor then sends the sub-region generator 208 the medical image and the sub-region selection information. Upon receiving the medical image and selection information, the sub-region generator 208 applies the sub-region size, shape and location information to the image to define the locations on the image associated with IPC functions specified for the sub-region. Additionally, the sub-region generator 208 may apply visual markings for the perimeter of the sub-region for the processor 204 to transmit to the PACS workstation 140 for display on the medical image. If the user selects an IPC function, the sub-region generator 208 receives the selected IPC function and applies the IPC function to the defined sub-region area. Furthermore, if the user specifies IPC function amounts, the sub-region generator 208 applies the IPC function amounts to the sub-region. For example, if a user selects a dark contrast for the sub-region, the sub-region generator 208 applies the IPC contrast function to the sub-region and changes the contrast to dark for the image within the sub-region. The sub-region generator 208 then sends the sub-region image with the applied contrast IPC function and contrast icon to the processor 204 for displaying in the PACS workstation 140.

In the example of FIG. 2, the IPC manager 150 includes the data transmitter 220 to forward sub-region display information to the PACS workstations 140 for display. The data transmitter 220 receives the information to forward from the processor 204. Upon receiving information from the processor 204, the data transmitter 220 forwards the information via connection 221 to the PACS workstations 140. Alternatively, the data transmitter 220 may forward the information directly to the PACS server 130 for display on another PACS workstation 140. The data transmitter 220 helps ensure the PACS workstation 140 receives the information. In cases where the information is not received, the data transmitter 220 may continue to resend the information until the information is received by the PACS workstation 140. Additionally, the data transmitter 220 may send control level information for establishing a link to a PACS workstation 140.

For example, if a PACS workstation 140 invokes a user interface with the sub-region tool, the processor 204 receives the network address of the PACS workstation 140 from the PACS server 130. The processor 204 may send one or more control messages to the PACS workstation 140 via the data transmitter 220 to establish a communication link such that the processor 204 may subsequently send sub-region display information and/or images within applied sub-region to the same workstation 140. In other example implementations, the data transmitter 220 may be responsible for sending sub-region information to the corresponding PACS workstations 140. In this case, the data transmitter 220 uses image information (e.g., DICOM header information) included in the sub-region information to send the sub-region information to the appropriate PACS workstation 140.

The IPC manager 150 includes a configurer 212 to enable users of the IPC manager 150 to specify criteria and/or configurations for applying IPC functions to image sub-regions. The configurer 212 connects to the PACS server 130 via the connection 213 for communicating sub-region display configuration information. The configurer 212 may interface with hanging protocols, perspectives, and/or DDPs within the PACS server 130 for displaying sub-regions in the user interface. Alternatively, the configurer 212 may be directly coupled to the PACS workstations 140 and store user specific IPC manager 150 configuration information in the temporary memory 214.

The configurer 212 may be integrated with the PACS server 130 such that a list of configuration options is stored within the configurer 212 and the options selected for certain users and/or user interfaces is are stored in the PACS server 130. A user accesses the configurer 212 through icons within the user interface such as, for example, a utilities icon that opens into a list of sub-region display options and/or sub-region configuration options.

The example configurer 212 enables a user to specify the type of sub-regions for display in the user interface and/or the type of sub-regions to display by medical image type. For example, a user may specify sub-regions for display in an upper lung area with a light contrast for all e-ray images of a chest area. The configurer 212 stores the sub-regions as an upper lung sub-region template. Then, when a PACS workstation 140 loads an x-ray image of a chest, the PACS server 130 queries the configurer 212 by sending the image type. In response the configurer 212 directs the processor 204 to load the upper lung sub-region template from the temporary memory 214, apply the IPC functions of the upper lung sub-regions to the chest image and display the chest image with the upper lung sub-regions.

The configurer 212 within the IPC manager 150 enables a user to specify line color preferences for highlighting sub-regions, line thickness preferences, and/or line display preferences for example. Furthermore, the configurer 212 provides functionality for a user to, for example, define sub-region shapes, default sub-region function parameter values, and/or IPC function types. The preferences, shapes, parameter values, and/or IPC functions may be stored per each user, per each PACS workstation 140, and/or per image type, for example. Additionally, the configurer 212 enables a user to specify if the IPC manager 150 is activated upon opening a user interface or by a user selecting an icon in the user interface.

While an example manner of implementing the IPC manager 150 of FIG. 1 has been illustrated in FIG. 2, one or more of the interfaces, data structures, elements, processes and/or devices illustrated in FIG. 2 may be combined, divided, rearranged, omitted, eliminated and/or implemented in any other way. For example, the example input receiver 202, the example processor 204, the example sub-region generator 208, the example configurer 212, and/or the example data transmitter 220 illustrated in FIG. 2 may be implemented separately and/or in any combination using, for example, machine accessible instructions executed by one or more computing devices and/or computing platforms (e.g., the example processing platform 800 of FIG. 8). Further, the example input receiver 202, the example processor 204, the example sub-region generator 208, the example configurer 212, the example data transmitter 220, and/or, more generally, the IPC manager 150 may be implemented by hardware, software, firmware and/or any combination of hardware, software and/or firmware. Thus, for example, any of the example input receiver 202, the example processor 204, the example sub-region generator 208, the example configurer 212, the example data transmitter 220, and/or, more generally, the IPC manager 150 can be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended claims are read to cover a purely software or firmware implementation, at least one of the example input receiver 202, the example processor 204, the example sub-region generator 208, the example configurer 212, the example data transmitter 220, and/or, the IPC manager 150 are hereby expressly defined to include a tangible medium such as a memory, DVD, CD, etc. storing such software or firmware. Further still, the example IPC manager 150 may include additional devices, servers, systems, networks, gateways, portals, and/or processors in addition to, or instead of, those illustrated in FIG. 2 and/or may include more than one of any or all of the illustrated devices, servers, networks, systems, gateways, portals, and/or processors.

Figure 3:
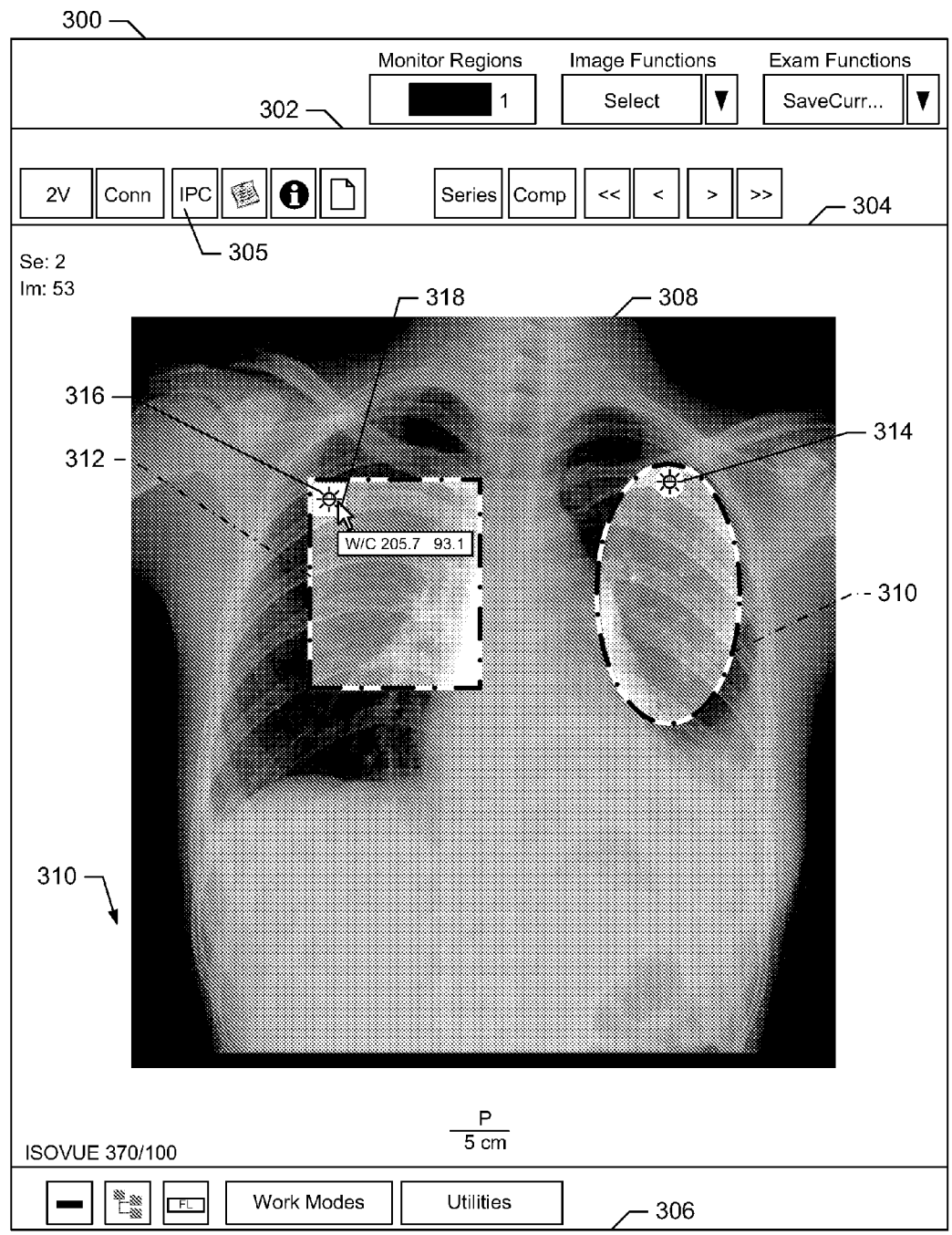
FIG. 3 shows an example user interface displaying a medical image with two image sub-regions managed by the example IPC manager of FIG. 2.

FIG. 3 shows an example user interface 300 displaying image sub-regions managed by the IPC manager 150 of FIG. 2. The user interface 300 includes tool bars 302, 304, and 306 that provide access to configuration menus, navigation tools, viewing tools, imaging applications, file management tools, etc. The tool bars 302, 304, and 306 may include additional icons and/or functionalities or less icons and/or functionalities shown. An IPC manager icon 305 is shown within the navigation tool bar 304. The IPC manager icon 305 activates the functionalities (e.g., a sub-region tool) of the IPC manager 150 upon a user selecting the IPC manager icon 305. Additionally, by selecting the IPC manager icon 305 a second time the IPC manager 150 and its associated functionalities may be deactivated.

The user interface 300 includes a display area 310 for displaying a medical image 308. Additionally, the display area 310 displays associated information regarding the medical image 308 including any information included in a file of the medical image 308 generated by the imaging modality 110 and/or the acquisition workstation. This information may include the type of imaging modality 110 used to generate the image, patient identification information, image creation date and time, patient medical information, etc.

In the example of FIG. 3, the medical image 308 shows an x-ray image of a chest region and includes sub-regions 310 and 312. The sub-regions 310 and 312 show different WC/WW IPC function amounts than the medical image 308. These different IPC function amounts enable a user to view tissue in the lung region (in the sub-regions 310 and 312) while viewing bone structures (outside the sub-regions 310 and 312) without having to view more than one medical image. For example, the image within the sub-region 310 is lighter and/or more exposed showing the tissue of a lung, while the area exterior to the sub-region 310 is darker or less exposed and shows the tissue as invisible. Though the user interface 300 shows two sub-regions 310 and 312, the user interface 300 may include additional sub-regions of any shapes and/or sizes. These additional sub-regions may overlap and/or may be nested within each other. Furthermore, the sub-regions 310 and 312 may include additional IPC functions.

The sub-region 310 is created by a user selecting the IPC manager icon 305 to display a list of sub-region creation and modification functionality. Within the list, a selection of an oval subregion enables the user to specify the sub-region 310 by moving a mouse cursor to place and size the oval on the desired location. The user may right-click on the mouse while the mouse cursor is position over the icon 314 or while the mouse cursor is positioned within the sub-region 310 to display a list of IPC functions. Upon selecting the WC/WW IPC function, the user selects the WC/WW amount. Upon receiving the sections, the IPC manager 150 displays the sub-region 310 with the modified image. Likewise, the sub-region 312 is created by a user selecting the IPC manager icon 305, selecting a rectangle shape, placing and sizing the sub-region 312, selecting the WC/WW IPC function, and selecting the WC/WW amount.

The perimeters of the sub-regions 310 and 312 are indicated by a dashed black and white line. In other example implementations, the perimeters may be indicated by color lines. The sub-region 310 is an oval shape positioned over a left lung area on the medical image 308 and includes an icon 314. The icon 314 indicates the WC/WW IPC function is applied to the sub-region 310. Additionally, the sub-region 312 is a rectangle shape positioned over a right lung area and includes an icon 316. The icon 316 indicates the WC/WW IPC function is applied to sub-region 310. If a user changes the size of the sub-region 310 and/or 312, the image area within the newly sized sub-region 310 and/or 312 receives the same respective IPC function and IPC function parameter amount as is the originally sized sub-region 310 and/or 312.

Although the sub-regions 310 and 312 both include WC/WW IPC functions, the sub-region 310 may have a different parameter value then the sub-region 312. For example, the user interface 300 includes a cursor 318 positioned over the icon 316 displaying a text box indicating the W/C IPC function amount for sub-region 312 (i.e., W/C 205.7 93.1). However, the sub-region 310 may include an IPC function parameter amount of 'W/C 201.2 93.1'.

Figure 4:
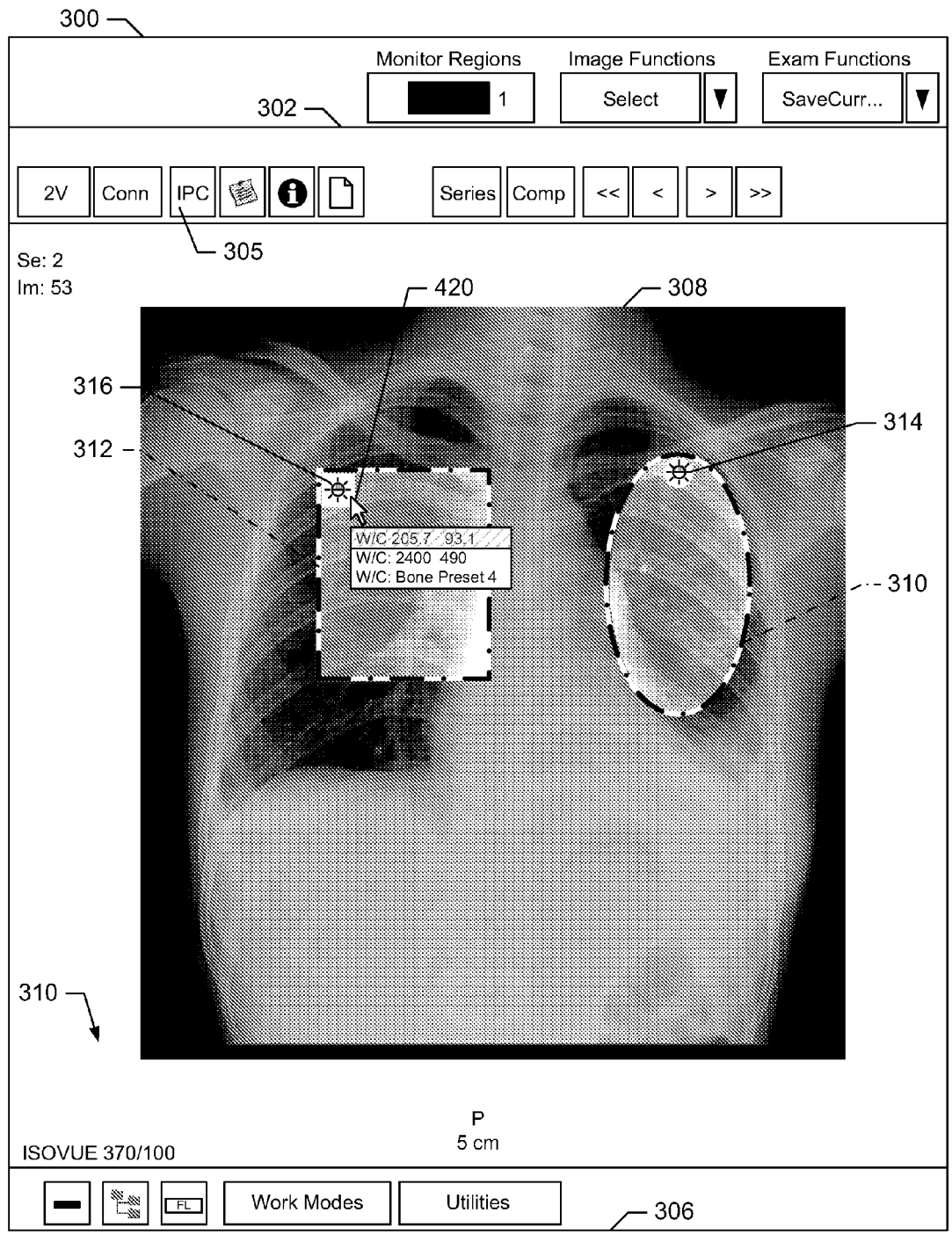
FIG. 4 shows the example user interface displaying the medical image and image sub-regions of FIG. 3 including selectable IPC function parameters managed by the IPC manager of FIG. 2.

FIG. 4 shows the example user interface 300 of FIG. 3 displaying the medical image 308 and sub-regions 310 and 312 of FIG. 3 including selectable IPC function parameters displayed in a toggle menu 420 managed by the IPC manager 150 of FIG. 2. The user interface 300 includes the tool bars 302, 304, and 306, the IPC manager icon 305, the icons 314 and 316, and the display area 310 of FIG. 3. The toggle menu 420 displays three WC/WW amounts, 'W/C: 205.7 93.1,' 'W/C: 2400 490,' and 'W/C: Bone Preset 4' with the 'W/C: 205.7 93.1' amount shown as currently selected.

The toggle menu 420 is displayed by a user selecting the icon 316 with the mouse cursor. The WC/WW amounts in the toggle menu 420 may be organized and/or displayed by the most previously selected WC/WW amounts or may be amounts configured by a user to be displayed for x-ray images for the WC/WW IPC function. The 'W/C: Bone Preset 4' shows a user has configured a WC/WW IPC function amount for the optimal viewing of bone structures in an x-ray image. For example, a selection of the 'W/C: Bone Preset 4' amount may change the image in the sub-region 312 such that the bones are prominently displayed behind a dark background. As a user scrolls through the IPC function amounts in the toggle menu 420 the image within the sub-region 312 may change by the amounts specified by the scrolled over IPC function amount. In other example implementations the toggle menu 420 may contain additional WC/WW IPC function amounts. Alternatively, the toggle menu 420 may enable a user to specify numerically or by a text description a WC/WW amount by inputting values from a keyboard.

Figure 5:
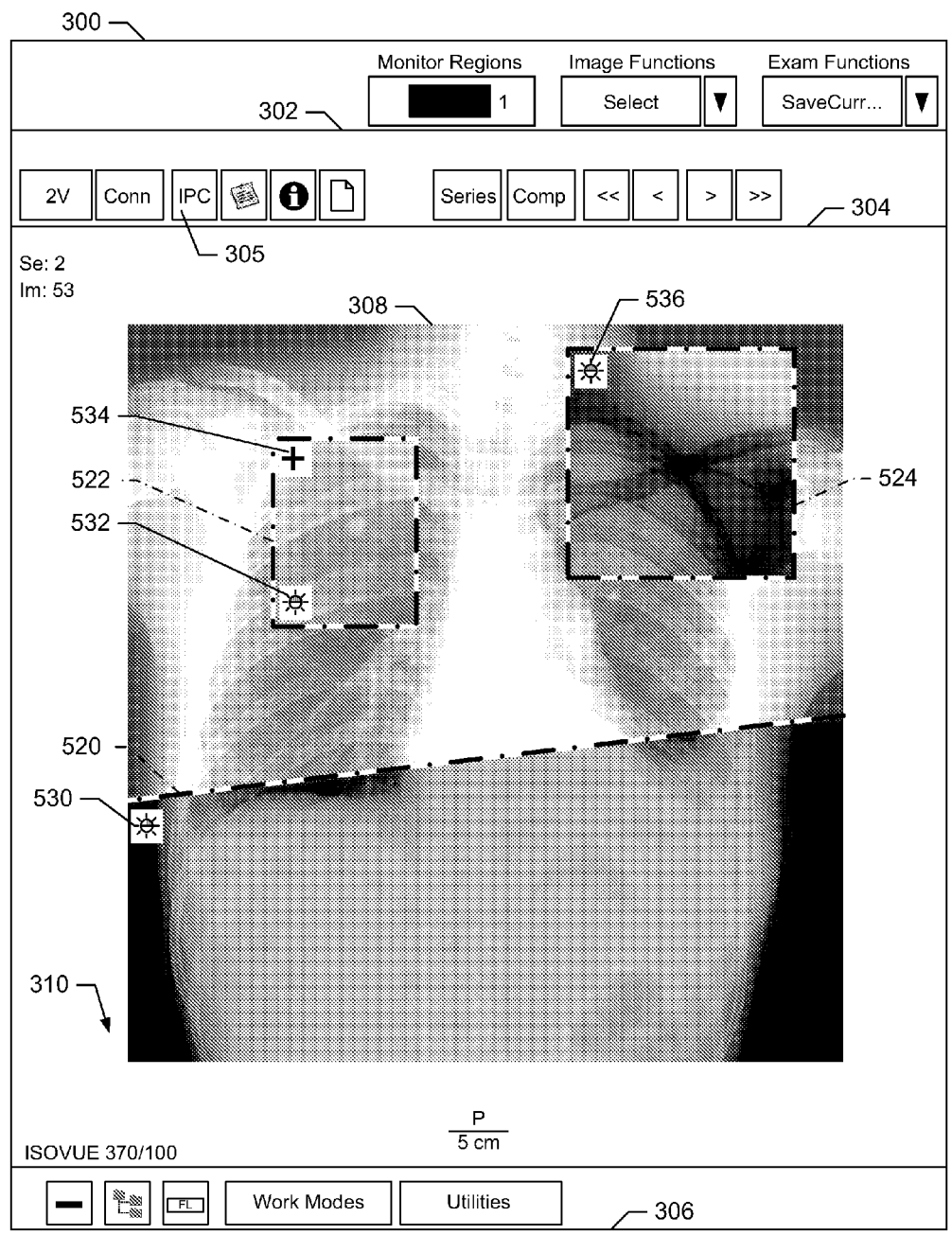
FIG. 5 shows the example user interface of FIG. 3 displaying a medical image with three image sub-regions managed by the example IPC manager of FIG. 2.

FIG. 5 shows the example user interface 300 of FIG. 3 displaying the medical image 308 with three sub-regions 520, 522, and 524 managed by the example IPC manager 150 of FIG. 2. The user interface 300 includes the tool bars 302, 304, and 306, the IPC manager icon 305, and the display area 310 of FIG. 3. The sub-regions 520, 522, and 524 display sections of the medical image 308 with different IPC functions. The sub-regions 522 and 524 are rectangular sub-regions with perimeters specified by dashed black and white lines.

The sub-region 520 is created by dragging a line from one perimeter location of the medical image 308 to another perimeter location of the medical image 308. The line connecting the two selected points on the perimeter is shown as a dashed black and white line. An icon 530 within the sub-region 520 indicates a WC/WW IPC function is applied to the sub-region 520. Additionally, the sub-region 520 is shown with a darker contrast enabling a clearer view of bone structures. Likewise, the sub-region 524 includes an icon 536 indicating a WC/WW IPC function is applied. The sub-region 524 shows a darker contrast with a different WC/WW amount than in the sub-region 520.

The sub-region 522 includes icons 532 and 534. The icon 532 indicates a WC/WW IPC function is applied while the icon 534 indicates a zoom IPC function is applied to the sub-region 522. The WC/WW IPC function in the sub-region 522 appears lighter in contrast than the sub-regions 520 and 524. This lighter contrast highlights the display of tissue. Furthermore, the sub-region 522 shows a magnification of the image within the sub-region 522. This magnification highlights a small growth (e.g., small grey circle in the center of the sub-region 522) within the tissue. By applying the WC/WW and zoom IPC functions to a single sub-region 522 of the medical image 308 a user may view the anatomy more clearly then by viewing a medical image with the WC/WW IPC function and a separate medical image of just the magnified sub-region. Additionally, a user may quickly create other sub-regions in the medical image 308 to search for other growths within the chest area.

Figure 6:
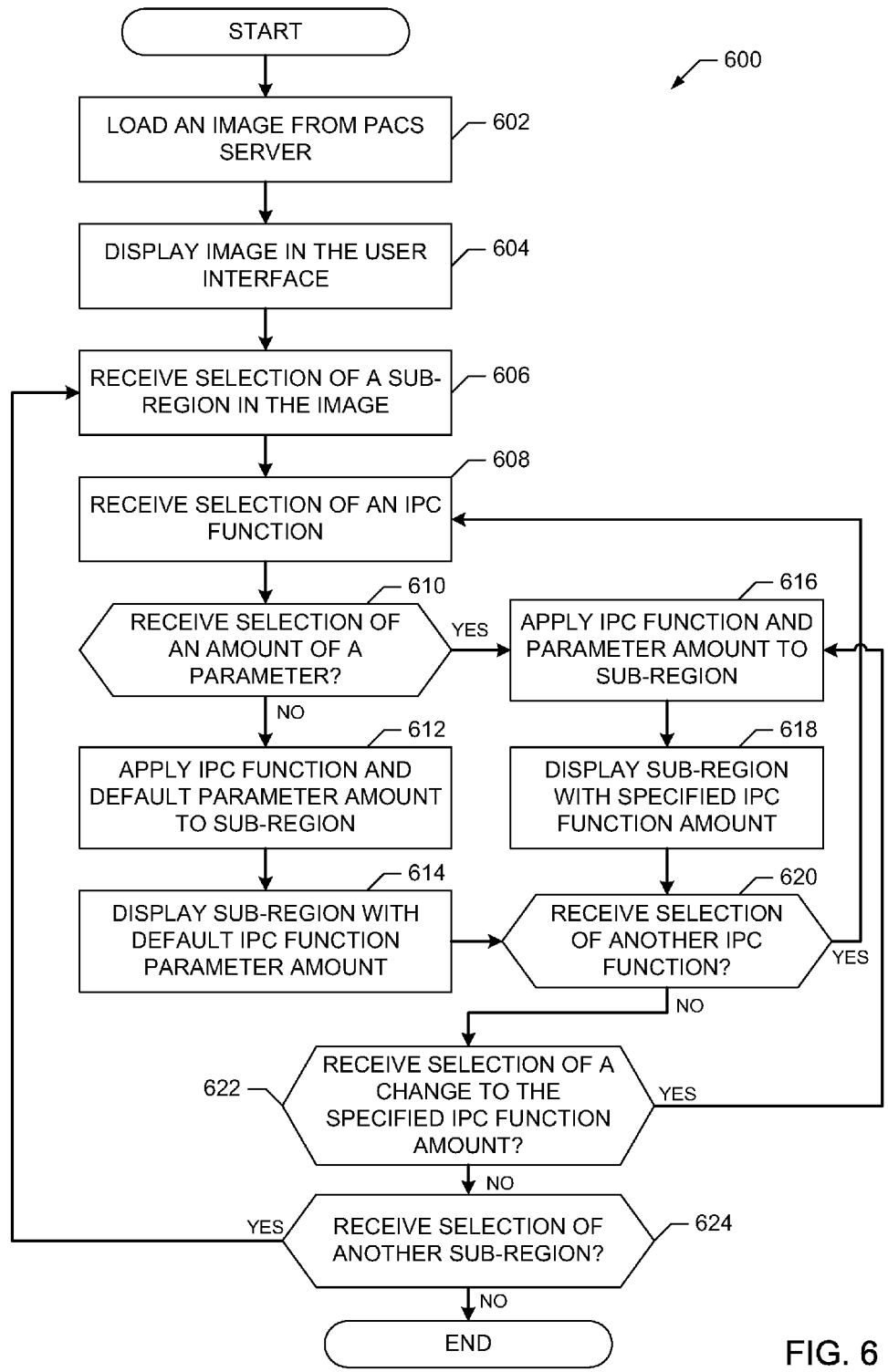
FIGS. 6 and 7 are flowcharts representative of example machine accessible instructions that may be executed by, for example, a processor to implement any portion or all of the example IPC manager of FIG. 2.
Figure 7:
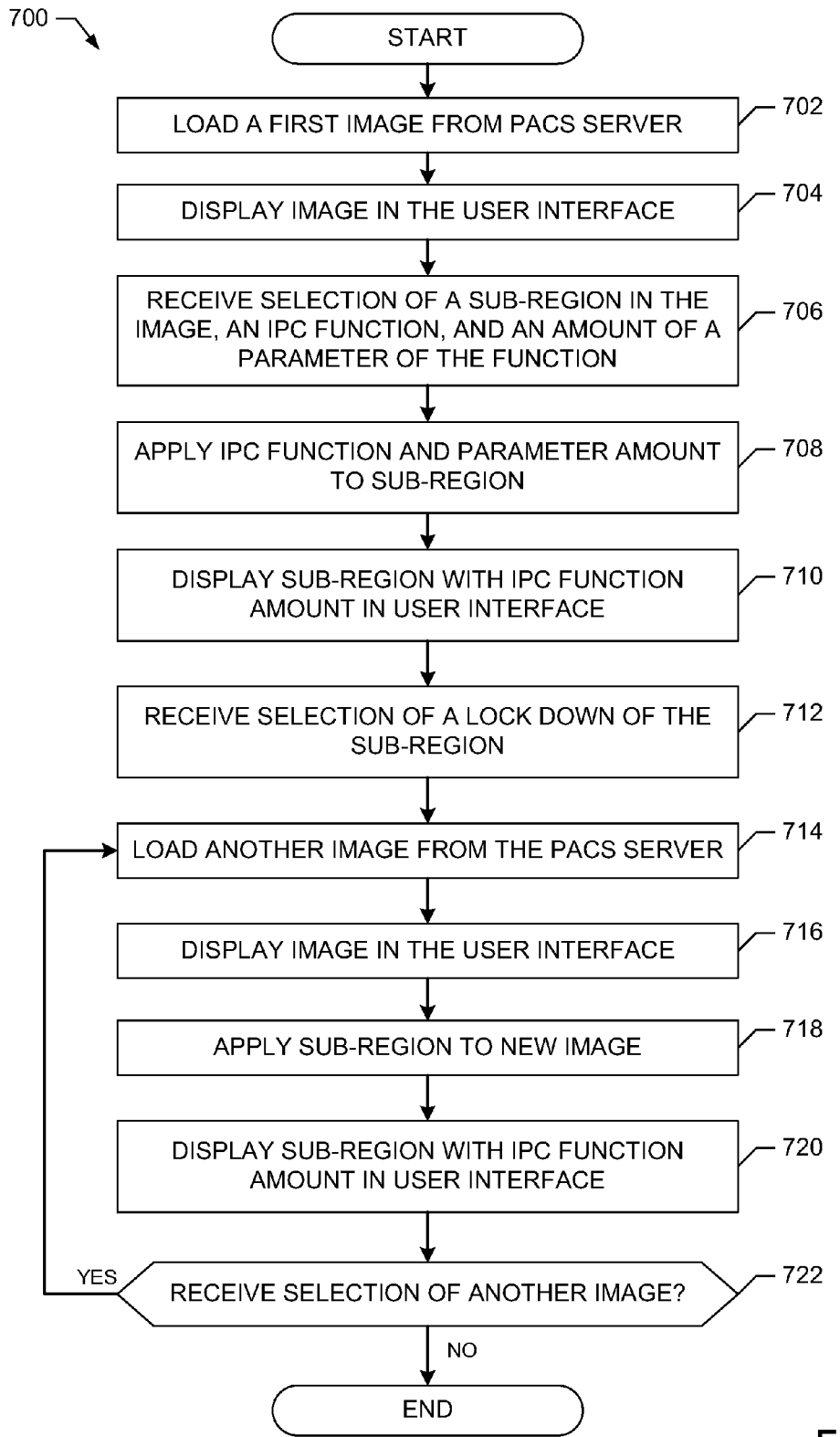

FIGS. 6 and 7 are flowcharts representative of example machine readable instructions that may be executed to apply IPC functions to image sub-regions in the IPC manager 150 of FIGS. 1 and 2. The example machine readable instructions may be executed using, for example, a processor system such as the system 800 of FIG. 8. However, one or more of the blocks depicted in the flowcharts may be implemented in any other manner, including by dedicated purpose circuitry, manual operations, etc. Additionally, although the example instructions are described with reference to the flowcharts of FIGS. 6 and 7, other methods to IPC functions to image sub-regions in tile IPC manager 150 may additionally or alternatively be used. For example, the order of execution of the blocks depicted in the flowcharts of FIGS. 6 and/or 7 may be changed, and/or some of the blocks described may be rearranged, eliminated, or combined.

The example instructions 600 represented by FIG. 6 may be performed to implement any or all of the example IPC manager 150 of FIGS. 1 and/or 2. The example instructions 600 may be executed at predetermined intervals (e.g., hourly, yearly, etc), in response to an occurrence of a predetermined event or trigger (e.g., the IPC manager 150 being activated upon opening a user interface), in response to a user request, or on any combination thereof.

The example instructions 600 of FIG. 6 begin when an image is loaded from the PACS server 130 to a user interface with a sub-region application (e.g., sub-region tool) on a PACS workstation 140 (block 602). Upon receiving the image, the user interface displays the image in the user interface (block 604). Additionally, the IPC manager 150 may receive the image from the PACS server 130. Next, the IPC manager 150 receives a selection of a subregion in the image (block 606). The selection may include the sub-region size, shape, and/or location within the image. Furthermore, the selection is made by a user of the PACS workstation placing and/or drawing a shape on the displayed image. Upon receiving a selection of the sub-region, the IPC manager 150 receives a selection of an IPC function for the selected sub-region (block 608).

Upon receiving a sub-region and a corresponding IPC function, the IPC manager 150 determines if there is a selection of a parameter amount for the IPC function (block 610). If a parameter amount is not specified, the IPC manager 150 applies a default parameter amount of the IPC function to the image specified by the sub-region (block 612). Next, the IPC manager 150 displays the sub-region with the default IPC function parameter amount in the image displayed in the user interface (block 614). Additionally, the IPC manager 150 may display an icon within the sub-region indicating the IPC function. Upon displaying the sub-region, the IPC manager 150 determines if another IPC function is selected (block 620).

If a parameter amount is specified when the IPC manager 150 determines if there is a selection of a parameter amount (block 610), the IPC manager 150 applies the selected IPC function and selected IPC function parameter amount to the sub-region (block 616). Next, the IPC manager 150 displays the sub-region with the selected IPC function parameter amount in the image displayed in the user interface (block 618). Upon displaying the sub-region, the IPC manager 150 determines if another IPC function is selected (block 620).

If the IPC manager 150 determines another IPC function is selected for the sub-region, the IPC manager 150 receives the selected function (block 608) and control proceeds through specifying a parameter amount (block 610-618). If another function is not selected, the IPC manager 150 determines if the parameter amount of an IPC function is changed (block 622). If an IPC function amount is changed, control returns to block 616 and the IPC manager 150 applies the changed parameter amount to the sub-region. If the IPC manager 150 does not receive a change to the IPC function parameter amount, the IPC manager 150 determines if another sub-region is selected (block 624). If another sub-region is selected, the IPC manager 150 receives the selected sub-region (block 606 and proceeds to apply one or more IPC functions to the newly selected sub-region (blocks 608-622).

If the IPC manager 150 determines another sub-region is not selected, the example instructions 600 end.

The example instructions 700 represented by FIG. 7 may be performed to implement any or all of the example IPC manager 150 of FIGS. 1 and/or 2. The example instructions 700 may be executed at predetermined intervals (e.g., hourly, yearly, etc), in response to an occurrence of a predetermined event or trigger (e.g., the IPC manager 150 being activated upon opening a user interface), in response to a user request, or on any combination thereof.

The example instructions 700 of FIG. 7 begin when a first image is loaded from the PACS server 130 of FIG. 1 to a user interface with a sub-region application (e.g., sub-region tool) on a PACS workstation 140 (block 702). Upon receiving the image, the user interface displays the image in the user interface (block 704). Next, the IPC manager 150 receives a selection of a sub-region in the image, a selection of all IPC function, and a selection of an IPC function amount (block 706). Alternatively, the IPC manager 150 may receive selections of a plurality of sub-regions and one or more IPC functions selected for each sub-region. Furthermore, for each IPC function selected a default IPC function amount is applied or an IPC function amount is selected. Next, the IPC manager 150 applies the selected IPC function and the selected (or default) IPC function amount to the selected sub-region (block 708) and displays the sub-region with the applied IPC function in the image in the user interface (block 710).

The example instructions 700 continue when the IPC manager 150 receives a lock down selection of the sub-region (block 712). Alternatively, the IPC manager 150 may receive selections of lock downs for a plurality of sub-regions. The lock down selection enables a user to scroll and/or select different images for display in the user interface with the IPC manager 150 applying the locked down sub-region to the newly displayed image.

Upon locking down the sub-region, a second image is loaded from the PACS server 130 on to the user interface (block 714). Next, the second image is displayed in the user interface on the PACS workstation 140 (block 716). The IPC manager 150 then applies the subregion and associated IPC function to the second image (block 718). Additionally, the IPC manager 150 may apply other locked sub-regions and respective IPC functions to the second image if a plurality of sub-regions is locked down in the first image. Upon applying the IPC function to the second image, the second image is displayed with the sub-region (block 720). Next, the IPC manager 150 determines if another image is selected to replace the second image (block 722). If another image is selected, the selected image is loaded from the PACS server 130 and the IPC manager 150 applies the sub-region to the newly selected image (blocks 714-720). Alternatively, new sub-regions may be created and locked down in the second image. If the IPC manager 150 determines another image is not selected, the example instructions 700 end.

Figure 8:
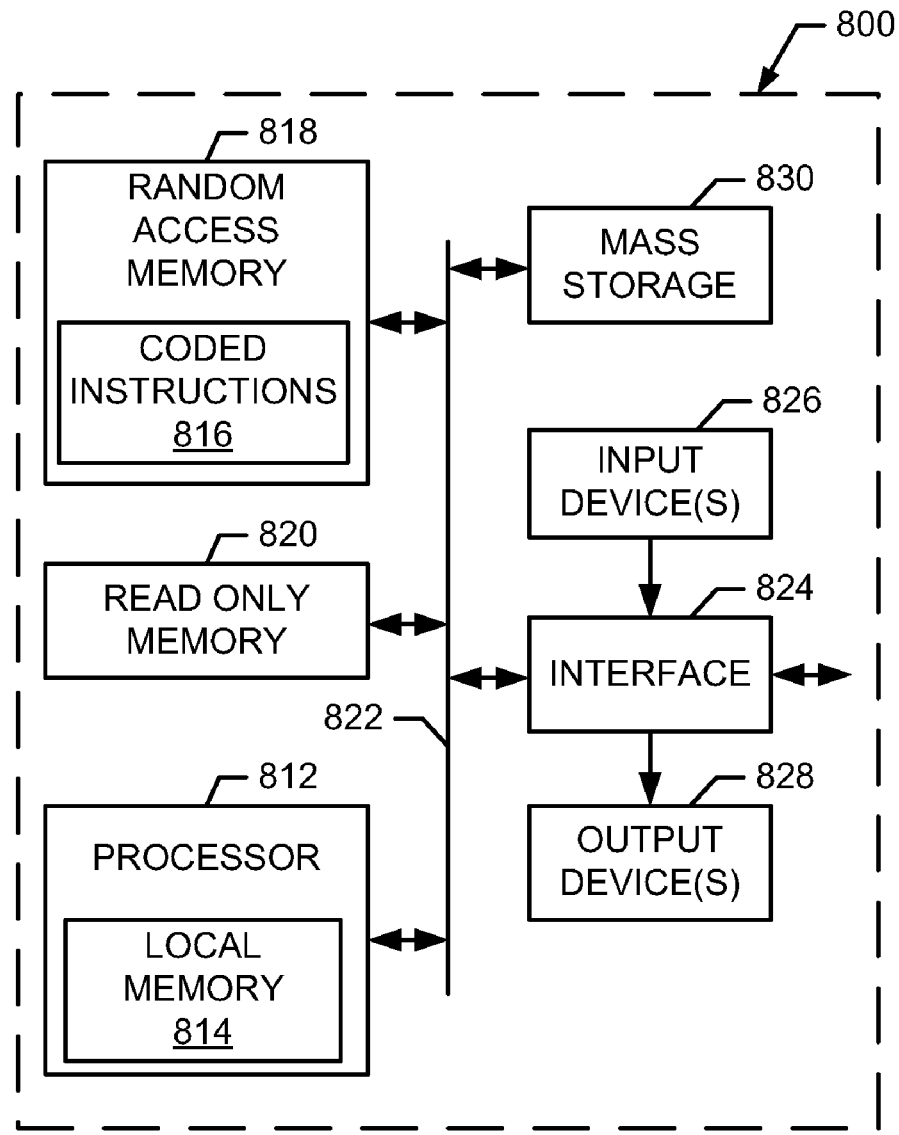
FIG. 8 is a schematic illustration of an example processor platform that may be used and/or programmed to implement the example IPC manager of FIG. 2 and/or to carry out applying image presentation context functions to image sub-regions and/or the example machine accessible instructions of FIGS. 6 and/or 7 to implement any or all of the example system and methods described herein.

FIG. 8 is a block diagram of an example computer system 800 capable of implementing the systems and methods disclosed herein. The computer 800 can be, for example, a server, a personal computer, an internet appliance, or any other type of computing device. Any or all of the example IPC manager 150 of FIGS. 1 and/or 2 may be implemented by the example computer 800.

The system 800 of the illustrated example includes a processor 812 such as a general purpose programmable processor. The processor 812 includes a local memory 814, and executes coded instructions 816 present in the local memory 814 and/or in another memory device. The coded instructions 816 may include some or all of the instructions represented in FIGS. 6 and/or 7. The processor 812 may be any type of processing unit, such as one or more microprocessors from the Intel® Centrino® family of microprocessors, the Intel® Pentium® family of microprocessors, the Intel® Itanium® family of microprocessors, the Intel® Core® family of microprocessors, and/or the Intel® XScale® family of processors. Of course, other processors from other families are also appropriate.

The processor 812 is in communication with a main memory including a volatile memory 818 and a non-volatile memory 820 via a bus 822. The volatile memory 818 may be implemented by Static Random Access Memory (SRAM), Synchronous Dynamic Random Access Memory (SDRAM), Dynamic Random Access Memory (DRAM), RAMBUS Dynamic Random Access Memory (RDRAM) and/or any other type of random access memory device. The non-volatile memory 820 may be implemented by flash memory and/or any other desired type of memory device. Access to the main memory 818, 820 is typically controlled by a memory controller.

The computer 800 also includes an interface circuit 824. The interface circuit 824 may be implemented by any type of interface standard, such as an Ethernet interface, a universal serial bus (USB), and/or a third generation input/output (3GIO) interface.

One or more input devices 826 are connected to the interface circuit 824. The input device(s) 826 permit a user to enter data and commands into the processor 812. The input device(s) can be implemented by, for example, a keyboard, a mouse, a touchscreen, a track-pad, a trackball, an isopoint and/or a voice recognition system.

One or more output devices 828 are also connected to the interface circuit 824. The output devices 828 can be implemented, for example, by display devices (e.g., a liquid crystal display, a cathode ray tube display (CRT)), by a printer and/or by speakers. The interface circuit 824, thus, typically includes a graphics driver card.

The interface circuit 824 also includes a communication device such as a modem or network interface card to facilitate exchange of data with external computers via a network (e.g., an Ethernet connection, a digital subscriber line (DSL), a telephone line, coaxial cable, a cellular telephone system, etc.).

The computer 800 also includes one or more mass storage devices 830 for storing software and data. Examples of such mass storage devices 830 include floppy disk drives, hard drive disks, compact disk drives and digital versatile disk (DVD) drives. The mass storage devices 830 may implement any or all of the example temporary memory 214. Additionally or alternatively, the volatile memory 818 may implement any or all of the example temporary memory 214.

At least some of the above described example methods and/or system are implemented by one or more software and/or firmware programs running on a computer processor. However, dedicated hardware implementations including, but not limited to, application specific integrated circuits, programmable logic arrays and other hardware devices can likewise be constructed to implement some or all of the example methods and/or apparatus described herein, either in whole or in part. Furthermore, alternative software implementations including, but not limited to, distributed processing or component/object distributed processing, parallel processing, or virtual machine processing can also be constructed to implement the example methods and/or apparatus described herein.

Certain example implementations contemplate methods, systems and computer program products on any machine-readable media to implement functionality described above. Certain example implementations may be implemented using an existing computer processor, or by a special purpose computer processor incorporated for this or another purpose or by a hardwired and/or firmware system, for example.

Certain example implementations include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

To the extent the above specification describes example components and functions with reference to particular standards and protocols, it is understood that the scope of this patent is not limited to such standards and protocols. For instance, each of the standards for internet and other packet switched network transmission (e.g., Transmission Control Protocol (TCP)/Internet Protocol (IP), User Datagram Protocol (UDP)/IP, HyperText Markup Language (HTML), HyperText Transfer Protocol (HTTP)) represent examples of the current state of the art. Such standards are periodically superseded by faster or more efficient equivalents having the same general functionality. Accordingly, replacement standards and protocols having the same functions are equivalents which are contemplated by this patent and are intended to be included within the scope of the accompanying claims.

Additionally, although this patent discloses example systems including software or firmware executed on hardware, it should be noted that such systems are merely illustrative and should not be considered as limiting. For example, it is contemplated that any or all of these hardware and software components could be embodied exclusively in hardware, exclusively in software, exclusively in firmware or in some combination of hardware, firmware and/or software. Accordingly, while the above specification described example systems, methods and articles of manufacture, the examples are not the only way to implement such systems, methods and articles of manufacture. Therefore, although certain example methods, apparatus and articles of manufacture have been described herein, the scope of coverage of this patent is not limited thereto. On the contrary, this patent covers all methods, apparatus and articles of manufacture fairly falling within the scope of the appended claims either literally or under the doctrine of equivalents.

What is claimed is:

1. A method of applying an image presentation context function to a medical image sub-region, the method comprising:
   receiving a selection of a first image sub-region within a first medical image associated with a first medical image type, the first medical image being displayed in a user interface;
   receiving a selection of a first image presentation context function and a selection of an amount of a parameter of the first image presentation context function for the first image sub-region;
   applying the first image presentation context function by the amount of the parameter of the first image presentation context function to the first image sub-region;
   displaying the first sub-region with the applied first image presentation context function within the first medical image;
   storing an indicator of the first image sub-region, the first image presentation context function, and the amount of the parameter of the first image presentation context function in association with the first medical image type;
   receiving a selection of a second medical image;
   if the second medical image is associated with the first medical image type:
      selecting a second image sub-region within the second medical image using the indicator of the first image-sub region, the second image sub-region corresponding to the first image sub-region;
      applying the first image presentation context function by the amount of the parameter of the first image presentation context function to the second image sub-region; and
      displaying the second sub-region with the applied first image presentation context function within the second medical image.

2. A method as defined in claim 1, further comprising:
   receiving a selection of a third image sub-region within the first medical image;
   receiving a selection of a second image presentation context function and a selection of an amount of a parameter of the second image presentation context function for the third image sub-region;
   applying the second image presentation context function by the amount of the parameter of the second image presentation context function to the third image sub-region; and
   displaying the third sub-region with the applied second image presentation context function within the first medical image.

3. A method as defined in claim 2, wherein the third image sub-region is at least one of overlapping with at least some of the first image sub-region, within the first image sub-region, or adjacent to the first image sub-region.

4. A method as defined in claim 1, wherein the image presentation context function is at least one of a zoom function, a window center/width function, a pan function, a filter function, a grayscale function, an invert color function, or a contrast function.

5. A method as defined in claim 4, wherein the amount of the parameter of the first image presentation context function is at least one of a zoom amount, a window center amount, a window width amount, a pan amount, a filter type, a filter amount, a grayscale amount, or a contrast amount.

6. A method as defined in claim 4, wherein the amount of the parameter is at least one of specified by a user, specified by a system developer, or specified by the first medical image type.

7. A method as defined in claim 1, wherein the selection of the first image sub-region includes at least one of placing a geometrical shape on the first medical image, defining an area within the geometrical shape as the first image sub-region, or drawing a perimeter on the first medical image defining an area within the perimeter as the first image sub-region.

8. A method as defined in claim 1, further comprising displaying an icon within the first image sub-region indicating the applied first image presentation context function upon displaying the first sub-region with the applied first image presentation context function within the first medical image.

9. A method as defined in claim 1, wherein the second sub-region of the second medical image is a similar size to the first sub-region of the first medical image.

10. A method as defined in claim 1, wherein the second sub-region of the second medical image is located in a similar position on the second medical image as the first sub-region of the first medical image on the first medial image.

11. A method as defined in claim 1, wherein the medical image is a medical image generated during one or more medical imaging procedures.

12. A method as defined in claim 1, further comprising:
   receiving a selection of a second image presentation context function and a
   selection of an amount of a parameter of the second image presentation context function for the first image sub-region;
   applying the second image presentation context function by the amount of the parameter of the second image presentation context function to the first image sub-region; and
   displaying the first sub-region with the applied second image presentation context function within the first medical image.

13. A method as defined in claim 1, further comprising:
   receiving a selection of the first image presentation context function and a selection of a second amount of a parameter of the first image presentation context function for the first image sub-region;
   replacing the amount by the second amount and applying the first image presentation context function by the second amount of the parameter of the first image presentation context function to the first image sub-region; and displaying the first sub-region with the applied second amount of the parameter of the first image presentation context function within the first medical image.

14. A method as defined in claim 13, further comprising:

receiving a selection of switching from the second amount of the parameter of the first image presentation context function to the amount of the parameter of the first image presentation context function; and displaying the first sub-region with the applied amount of the parameter of the first image presentation context function within the first medical image.

15. An image presentation context system applying an image presentation context function to a medical image sub-region, the system comprising:

an input receiver to receive:
   a selection of a first image sub-region within a first medical image associated with a first medical image type, a selection of a first image presentation context function, and an amount of a parameter of the first image presentation context function for the first image sub-region; and
   a selection of a second medical image;

a memory to store an indicator of the first image sub-region, the first image presentation context function, and the amount of the parameter of the first image presentation context function in association with the first medical image type;

an image presentation context generator to:
   apply the first image presentation context function by the amount of the parameter of the first image presentation context function to the first image sub-region; and
   if the second medical image is associated with the first medical image type, to:
      select a second image sub-region within the second medical image using the indicator of the first image sub-region, the second image sub-region corresponding to the first image sub-region; and
      apply the first image presentation context function by the amount of the parameter of the first image presentation context function to the second image sub-region.

16. An image presentation context system as defined in claim 15, further comprising:

a display system including a user interface to display:
   a first medical image and the first image sub-region with the applied first image presentation context function within the first medical image in the user interface; and
   a second medical image and the second image sub-region with the applied first image presentation context function within the second medical image, wherein the second medical image replaces the first medical image in the user interface.

17. An image presentation context system as defined in claim 16, wherein the display system displays an icon within the first image sub-region indicating the applied first image presentation context function upon displaying the first sub-region with the applied first image presentation context function within the first medical image.

18. An image presentation context system as defined in claim 15, wherein the second sub-region of the second medical image is a similar size to the first sub-region of the first medical image.

19. An image presentation context system as defined in claim 15, wherein the second sub-region of the second medical image is located in a similar position on the second medical image as the first sub-region of the first medical image on the first medial image.

20. An image presentation context system as defined in claim 15, wherein the input receiver receives a selection of a plurality of image sub-regions within the first medical image and receives a selection of an image presentation context function and a selection of an amount of a parameter of the second image presentation context function for the corresponding image sub-region.

21. An image presentation context system as defined in claim 20, wherein the image presentation context generator applies the image presentation context function by the amount of the parameter of the image presentation context function to the corresponding image sub-region.

22. An image presentation context system as defined in claim 20, wherein a display system displays the corresponding sub-region with the applied image presentation context function within the first medical image.

23. An image presentation context system as defined in claim 15, wherein the image presentation context function is at least one of a zoom function, a window center/width function, a pan function, a filter function, a grayscale function, an invert color function, or a contrast function.

24. An image presentation context system as defined in claim 23, wherein the amount of the parameter of the first image presentation context function is at least one of a zoom amount, a window center amount, a window width amount, a pan amount, a filter type, a filter amount, a grayscale amount, or a contrast amount.

25. An image presentation context system as defined in claim 23, wherein the amount of the parameter is at least one of specified by a user, specified by a system developer, or specified by the first medical image type.

26. An image presentation context system as defined in claim 15, wherein the selection of the first image sub-region includes at least one of placing a geometrical shape on the first medical image, defining an area within the geometrical shape as the first image sub-region, or drawing a perimeter on the first medical image defining an area within the perimeter as the first image sub-region.

27. An image presentation context system as defined in claim 15, wherein the medical image is a medical image generated during one or more medical imaging procedures.

28. An image presentation context system as defined in claim 15, wherein the input receiver receives a selection of the first image presentation context function and a selection of a second amount of a parameter of the first image presentation context function for the first image sub-region and receives a selection of switching from the second amount of the parameter of the first image presentation context function to the amount of the parameter of the first image presentation context function.

29. An image presentation context system as defined in claim 28, wherein the sub-region generator replaces the amount by the second amount and applies the received first image presentation context function by the second amount of the parameter of the first image presentation context function to the first image sub-region.

30. A tangible machine accessible medium having instructions stored thereon that, when executed, cause a machine to:

receive a selection of a first image sub-region within a first medical image associated with a first medical image type, the first medical image being displayed in a user interface;

receive a selection of a first image presentation context function and a selection of an amount of a parameter of the first image presentation context function for the first image sub-region;

apply the first image presentation context function by the amount of the parameter of the first image presentation context function to the first image sub-region;

display the first sub-region with the applied first image presentation context function within the first medical image;

store an indicator of the first image sub-region, the first image presentation context function, and the amount of the parameter of the first image presentation context function in association with the first medical image type;

if the second medical image is associated with the first medical image type:

select a second image sub-region within the second medical image using the indicator of the first image sub-region, the second image sub-region corresponding to the first image sub-region;

apply the first image presentation context function by the amount of the parameter of the first image presentation context function to the second image sub-region; and display the second sub-region with the applied first image presentation context function within the second medical image.

31. A machine accessible medium as defined in claim 30, wherein the machine readable instructions cause the machine to:

receive a selection of a third image sub-region within the first medical image;

receive a selection of a second image presentation context function and a selection of an amount of a parameter of the second image presentation context function for the third image sub-region;

apply the second image presentation context function by the amount of the parameter of the second image presentation context function to the third image sub-region; and display the third sub-region with the applied second image presentation context function within the first medical image.

32. A machine accessible medium as defined in claim 31, wherein the third image sub-region is at least one of overlapping with at least some of the first image sub-region, within the first image sub-region, or adjacent to the first image sub-region.

33. A machine accessible medium as defined in claim 30, wherein the image presentation context function is at least one of a zoom function, a window center/width function, a pan function, a filter function, a grayscale function, an invert color function, or a contrast function.

34. A machine accessible medium as defined in claim 30, wherein the machine readable instructions cause the machine to display an icon within the first image sub-region by indicating the applied first image presentation context function upon displaying the first sub-region with the applied first image presentation context function within the first medical image.

35. A machine accessible medium as defined in claim 30, wherein the machine readable instructions cause the machine to:

receive a selection of a second image presentation context function and a selection of an amount of a parameter of the second image presentation context function for the first image sub-region;

apply the second image presentation context function by the amount of the parameter of the second image presentation context function to the first image sub-region; and display the first sub-region with the applied second image presentation context function within the first medical image.

36. A machine accessible medium as defined in claim 30, wherein the machine readable instructions cause the machine to:

receive a selection of the first image presentation context function and a selection of a second amount of a parameter of the first image presentation context function for the first image sub-region;

replace the amount by the second amount and apply the first image presentation context function by the second amount of the parameter of the first image presentation context function to the first image sub-region; and display the first sub-region with the applied second amount of the parameter of the first image presentation context function within the first medical image.

37. A machine accessible medium as defined in claim 36, wherein the machine readable instructions cause the machine to:

receive a selection of switching from the second amount of the parameter of the first image presentation context function to the amount of the parameter of the first image presentation context function; and display the first sub-region with the applied amount of the parameter of the first image presentation context function within the first medical image.

* * * * *

UNITED STATES PATENT AND TRADEMARK OFFICE
CERTIFICATE OF CORRECTION

PATENT NO. : 8,229,193 B2  
APPLICATION NO. : 12/203682  
DATED : July 24, 2012  
INVENTOR(S) : Novatzky et al.

It is certified that error appears in the above-identified patent and that said Letters Patent is hereby corrected as shown below:

In Column 6, Line 62, delete "Such" and insert -- such --, therefor.

In Column 7, Line 61, delete "Tlhe" and insert -- The --, therefor.

In Column 10, Line 6, delete "tile IPC" and insert -- the IPC --, therefor.

In Column 11, Line 22, delete "temporally" and insert -- temporary --, therefor.

In Column 11, Line 24, delete "memory" and insert -- memory. --, therefor.

In Column 11, Line 61, delete "zoom/pall" and insert -- zoom/pan --, therefor.

In Column 13, Line 44, delete "is are stored" and insert -- are stored --, therefor.

In Column 13, Lines 65-66, delete "preferences" and insert -- preferences, --, therefor.

In Column 15, Line 7, delete "than the" and insert -- then the --, therefor.

In Column 17, Line 4, delete "tile" and insert -- the --, therefor.

In Column 18, Line 17, delete "all IPC" and insert -- an IPC --, therefor.

Signed and Sealed this  
Fifth Day of February, 2013

Teresa Stanek Rea  
*Acting Director of the United States Patent and Trademark Office*